United States Patent
Yu et al.

(10) Patent No.: US 6,447,441 B1
(45) Date of Patent: *Sep. 10, 2002

(54) NON-INVASIVE FLOW INDICATOR FOR A ROTARY BLOOD PUMP

(75) Inventors: Yih-Choung Yu, Pittsburgh; Kirk A. Lehmann, Library; John Chiasson, Pittsburgh; Wayne P. Griffin, Cranberry, all of PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 19 days.

This patent is subject to a terminal disclaimer.

(21) Appl. No.: 09/692,900

(22) Filed: Oct. 20, 2000

Related U.S. Application Data

(63) Continuation of application No. 09/130,617, filed on Aug. 7, 1998, now Pat. No. 6,135,943.

(51) Int. Cl.[7] .................................................. A61M 1/10
(52) U.S. Cl. ......................................................... 600/16
(58) Field of Search ............................ 600/16, 17, 18; 623/3

(56) References Cited

U.S. PATENT DOCUMENTS 4,955,856 A * 9/1990 Philips ........................ 607/16

* cited by examiner

*Primary Examiner*—Scott M. Getzow
(74) *Attorney, Agent, or Firm*—Ansel M. Schwartz

(57) ABSTRACT

An apparatus for non-invasive flow indication through a rotary blood pump. The apparatus includes a blood pump adapted for implantation into a patient. The blood pump has a moving mechanism which contacts blood and imparts energy to the blood to move the blood in the patient at a desired flow rate. The apparatus a mechanism for causing the moving mechanism to move the blood. The causing mechanism is engaged with the moving mechanism. The causing mechanism receiving energy to power the causing mechanism. The apparatus comprises a sensorless flow indicator connected to the blood pump to identify the flow of blood through the pump based only on an energy balance between the energy imparted to the blood by the moving mechanism and the energy received by the causing mechanism. A method for determining blood flow in a patient. The method includes the steps of providing energy to a blood pump implanted in a patient to operate the pump. Then there is the step of imparting energy to blood in the patient with the blood pump at a desired flow rate. Next there is the step of identifying the flow rate only by balancing the energy imparted to the blood with energy provided to the pump.

17 Claims, 5 Drawing Sheets

NON-INVASIVE FLOW INDICATOR FOR A ROTARY BLOOD PUMP

This application is a continuation of U.S. application Ser. No. 09/130,617, filed Aug. 7, 1998, now U.S. Pat. No. 6,135,943, issued Oct. 24, 2000.

FIELD OF THE INVENTION

The present invention is related to a rotary blood pump. More specifically, the present invention is related to an implantable centrifugal blood pump in which the blood flow through the pump can be identified without any invasive sensor.

BACKGROUND OF THE INVENTION

One concern associated with the implantation of a blood pump is the clotting of blood due to the presence of the pump in the blood circulatory stream. Any edge or crack or protrusion, for instance, that contacts the blood flow could serve as a location where blood could collect and clot, or cause disruption of the blood and result in blood clotting.

To minimize the possibility of a blood clot, it is desirable to minimize edges or protrusions present in the blood flow path. One approach to meeting this constraint is to avoid the use of any sensor that would introduce an edge or protrusion in the blood flow path. However, it is also important to know the flow of blood through the pump. It is thus desirable to be able to identify the flow of blood through an implanted pump without the presence of sensors in the blood flow path.

More problematic, the presence of sensors in an implanted pump will increase the need for separate wires, or connections to the sensors, through the patient along which the signal integrity must be reliably maintained. Because the implanted pump and supporting wiring for current to power the pump are already quite intrusive, it is desired to avoid any additional wires having to be present to connect to the pump through the patient. For this reason, it is desired not to need sensors and thus additional associated wires extending from the sensors through the patient.

The present invention provides for the identification of flow through the implanted pump in the heart without the need for any flow sensors. When a bi-ventricular assist is needed, this invention can be used to regulate the pump flow rate on both sides of the heart to ensure balanced device outputs.

SUMMARY OF THE INVENTION

The present invention pertains to an apparatus for moving blood in a patient. The apparatus comprises a blood pump adapted for implantation into a patient. The blood pump has a moving mechanism which contacts blood and imparts energy to the blood to move the blood in the patient at a desired flow rate. The apparatus comprises a mechanism for causing the moving mechanism to move the blood. The causing mechanism is engaged with the moving mechanism. The causing mechanism receives energy to power the causing mechanism. The apparatus comprises a flow indicator connected to the blood pump to identify the flow of blood through the pump based only on an energy balance between the energy imparted to the blood by the moving mechanism and the energy received by the causing mechanism.

The present invention pertains to a method for determining blood flow in a patient. The method comprises the steps of providing energy to a blood pump implanted in a patient to operate the pump. Then there is the step of imparting energy to blood in the patient with the blood pump at a desired flow rate. Next there is the step of identifying the flow rate only by balancing the energy imparted to the blood with energy provided to the pump.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
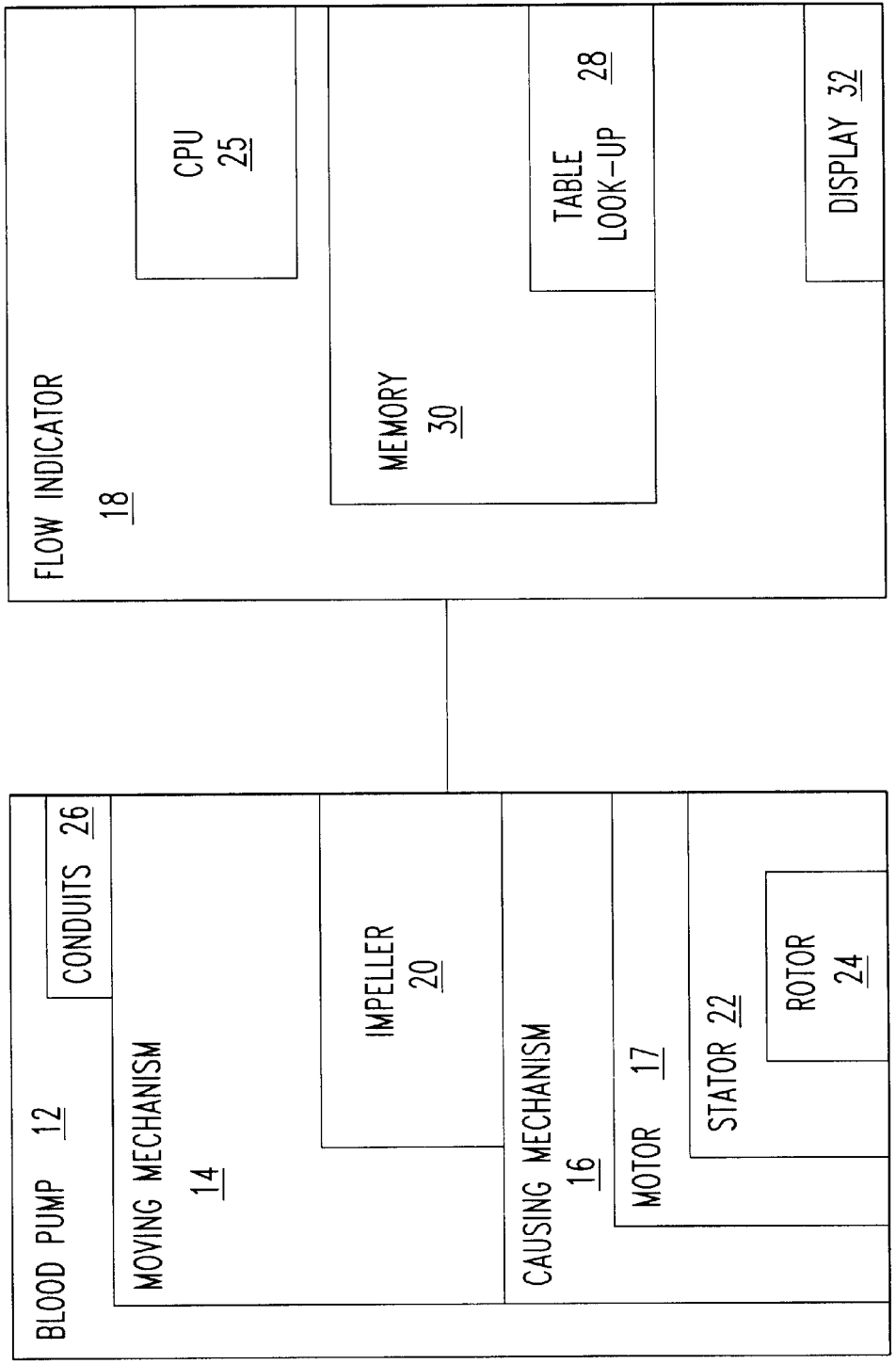
FIG. 1 is a schematic representation of an apparatus of the present invention.

Referring now to the drawings wherein like reference numerals refer to similar or identical parts throughout the several views, and more specifically to FIG. 1 thereof, there is shown an apparatus 10 for moving blood in a patient. The apparatus 10 comprises a blood pump 12 adapted for implantation into a patient. The blood pump 12 has a moving mechanism 14 which contacts blood and imparts energy to the blood to move the blood in the patient at a desired flow rate. The apparatus 10 comprises a mechanism for causing the moving mechanism 14 to move the blood. The causing mechanism 16 is engaged with the moving mechanism 14. The causing mechanism 16 receiving energy to power the causing mechanism 16. The apparatus 10 comprises a flow indicator 18 connected to the blood pump 12 to identify the flow of blood through the pump 12 based only on an energy balance between the energy imparted to the blood by the moving mechanism 14 and the energy received by the causing mechanism 16.

Preferably, the pump 12 is a rotary pump 12 such as a centrifugal pump 12 having a motor 17. The energy powering the causing mechanism 16 is preferably current and wherein the flow indicator 18 identifies the flow of blood with the current and speed of the motor 17 based on the energy balance between the energy imparted to the blood by the moving mechanism 14 and the energy received by the causing mechanism 16.

The moving mechanism 14 preferably includes an impeller 20. Preferably, the causing mechanism 16 includes a brushless DC motor 17. The motor 17 preferably includes a stator 22 and a rotor 24 disposed in the stator 22. The impeller 20 connected to the rotor 24. The motor 17 is preferably a three-phase permanent magnetic brushless DC motor 17.

Preferably, the flow rate Q of the blood through the pump 12 is defined by $$Q = \frac{1.5 \cdot K^* \cdot I - J \cdot \frac{d\omega}{dt} - B \cdot \omega}{K_1 \cdot \sqrt{\omega} + K_2 \cdot \omega^2},$$

where B is the viscous friction coefficient, $K_1$ and $K_2$ are constant coefficients, J is the motor's 17 inertia, I is the current amplitude, and $\omega$ is the rotor 24 angular velocity. $K^* = N_p \cdot K_B$ where $N_p$ is the number of pole pairs and $K_B$ is back-emf constant.

Preferably, the flow indicator 18 can detect retrograde flow; wherein, the pump 12 includes conduits 26 and the flow indicator 18 can detect kinking in the conduits.

Preferably, the flow indicator utilizes a curve fit to identify flow. The flow indicator preferably utilizes a table look up 28 based on the curve fit to identify blood flow.

The present invention pertains to a method for determining blood flow in a patient. The method comprises the steps of providing energy to a blood pump 12 implanted in a patient to operate the pump 12. Then there is the step of imparting energy to blood in the patient with the blood pump 12 at a desired flow rate. Next there is the step of identifying the flow rate only by balancing the energy imparted to the blood with energy provided to the pump 12.

Preferably, the providing step includes the step of providing current to a centrifugal blood pump 12 and the identifying step includes the step of measuring the current and speed of the pump 12. The flow indicator identifies the flow rate preferably according to $$Q = \frac{1.5 \cdot K^* \cdot I - J \cdot \frac{d\omega}{dt} - B \cdot \omega}{K_1 \cdot \sqrt{\omega} + K_2 \cdot \omega^2},$$

where B is the viscous friction coefficient, $K_1$ and $K_2$ are constant coefficients, J is the motor's inertia, I is the current amplitude, and $\omega$ is the rotor 24 angular velocity. $K^*$ is as previously defined.

In the operation of the preferred embodiment, an implantable rotary blood pump, such as the AB-180 centrifugal pump, well known in the art, is surgically implanted into a patient, as is well known in the art. Current from a power source is provided to the motor 17 of the pump 12 through wires, as is well known in the art. If the current provided to the stator 22 of the pump 12 is monitored so it is known and provided to a flow indicator 18 having a CPU. The current causes the stator 22 to become energized and create an electromagnetic field which turns the rotor 24 positioned within the stator 22, as is well known in the art. The rotor 24 is turned by the action of the current and the stator 22, which in turn causes the impeller 20 connected to the rotor 24 to rotate. The impeller 20 is disposed within a blood flow path connected to the left atrium of the heart through conduits 26 which receive blood from the heart and return the blood to the circulatory system. The blood from the heart is moved by the action of the impeller 20.

As the impeller 20 turns, it pushes the blood forward, imparting energy to the blood. The energy loss of the impeller 20 is an energy gain in the blood and essentially balances with the current which provides energy into the stator 22. The speed with which the rotator 24 turns is related to the amount of force used to move the blood. Thus, the current provided to the stator 22 identifies the amount of energy provided to the pump and the speed by which the impeller 20 turns identifies the amount of energy provided by the pump to the blood. Ideally, the amount of energy provided to the pump is equal to the amount of energy provided to the blood. The speed of the rotor 24 is identified through the back emf which is also detected from the pump, as is well known in the art.

From the current and the speed, the equation $$Q = \frac{1.5 \cdot K^* \cdot I - J \cdot \frac{d\omega}{dt} - B \cdot \omega}{K_1 \cdot \sqrt{\omega} + K_2 \cdot \omega^2},$$

identifies the volumetric flow rate of the blood.

The CPU 25 of the flow indicator 18 takes the current and the speed, through the back emf, and determines a corresponding flow from a table look up 28 in a memory 30 of the flow indicator. The flow is then displayed on a display 32 for the surgeon to be informed of the flow of blood through the pump 12. The surgeon then changes, if desired, the level of speed provided to the pump to control the speed of the impeller 20 and thus the flow of blood through the pump 12. If the current and speed indicate that the flow is too high at a given time, then the surgeon can choose to decrease the speed to a desired level to slow blood flow. Alternatively, if the current and speed indicate that the flow is too low at a given time, the surgeon can choose to increase the speed to a desired level to increase the flow of blood through the pump. This could also be accomplished in a closed loop control manner to achieve the desired volumetric flow through the pump. The flow indicator 18 with the aforesaid equation based on the current and speed identifies the flow of blood through the pump 12 to the surgeon so the surgeon can properly control the flow of blood through the pump 12 in the patient. By adjusting the speed of the pump, the current is adjusted. But current corresponds to the load of blood being pushed by the impeller 20. Since it is the flow that is the end result the surgeon desires to control, it is the speed that the surgeon reviews and manipulates. No sensor is required to be present within the patient's chest for the blood flow through the pump to be identified.

Figure 2:
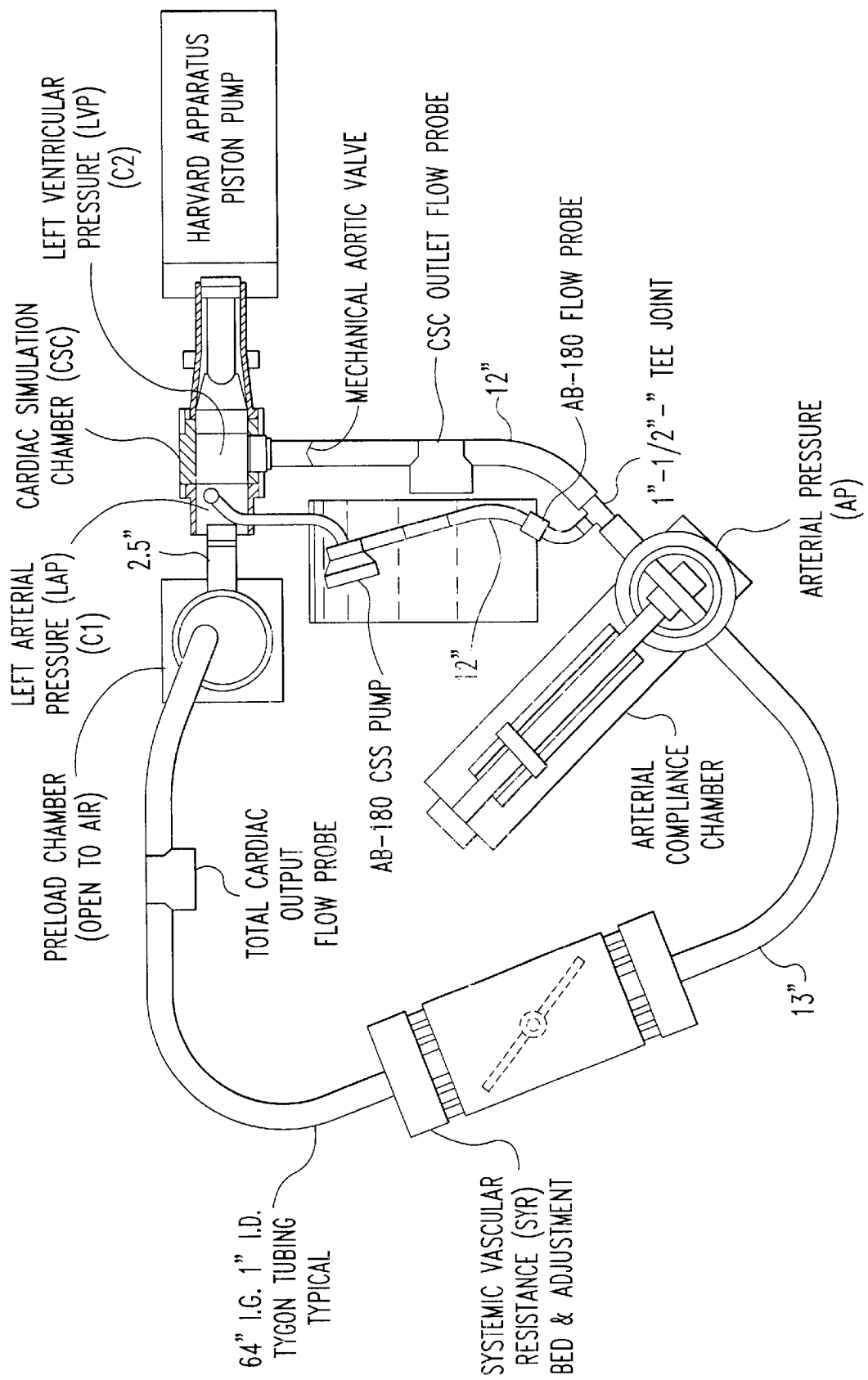
FIG. 2 is a schematic representation of the experimental setup to identify the flow.

As shown in FIG. 2, the AB-180 rotary blood pump speed is controlled by the ML4411 Sensorless Spindle Motor Controller from Micro Linear, Inc. The pin configuration is available from Micro Linear, Inc., incorporated by reference herein. The motor stator current feeds back to the controller at the 12th pin ($I_{SENSE}$) on the chip. The stator current signal used for flow estimation was obtained by amplifying this signal (in volts) and calibrating it to the actual current reading. The motor speed was measured at the 20th pin (RC) on the chip. The voltage signal at this pin is directly proportional to the speed.

The AB-180 centrifugal rotary blood pump is powered by a three-phase permanent magnetic brushless dc motor (BLDC). From the law of energy conservation, the electromagnetic energy, $W_{EM}$, transferred to the rotor from the external power source provides the mechanical energy stored in the mass, $W_{MS}$, the mechanical energy loss due to friction, $W_{ML}$, and the fluid energy for the pump, $W_p$, [P. C. Krause, O. Wasynczuk, and S. D. Sudhoff, *Analysis of Electric Machinery*, IEEE Press, 1995, pp. 13–29, incorporated by reference herein]. This relationship can be written as $$W_{EM} = W_{MS} + W_{ML} + W_p. \tag{1}$$

For a three-phase motor, the induced electromechanical energy, $W_{EM}$, can be written as $$W_{EM} = \int_0^t (e_{as} \cdot i_{as} + e_{bs} \cdot i_{bs} + e_{cs} \cdot i_{cs}) \cdot d\xi, \tag{2}$$

where $e_{as}$, $e_{bs}$, and $e_{cs}$ are the voltages in the stator induced by the magnetic field of the rotor, and $i_{as}$, $i_{bs}$, and $i_{cs}$ are the stator currents. By Faraday's law, the voltages, $e_{as}$, $e_{bs}$, and $e_{cs}$, are induced by the changing flux linkage of the rotor's magnetic field in the stator windings. For the stator with sinusoidal windings, the steady state flux linkage in each stator phase due to the rotor's magnetic field is [Ibid. pp. 500, incorporated by reference herein]

$$\begin{bmatrix} \varphi_a \\ \varphi_b \\ \varphi_c \end{bmatrix} = K_B \times \begin{bmatrix} \sin(N_P \cdot \omega \cdot t) \\ \sin\left(N_P \cdot \omega \cdot t - \dfrac{2\pi}{3}\right) \\ \sin\left(N_P \cdot \omega \cdot t + \dfrac{2\pi}{3}\right) \end{bmatrix}, \quad (3)$$

where $K_B$ is the back EMF constant in V·sec/rad, $N_p$ is the number of pole pairs of the rotor, and $\omega$ is the rotor angular velocity in rad/sec. The induced voltages are then $$\begin{bmatrix} e_{as} \\ e_{bs} \\ e_{cs} \end{bmatrix} = \dfrac{d}{dt}\begin{bmatrix} \varphi_a \\ \varphi_b \\ \varphi_c \end{bmatrix} = N_P \cdot \omega \cdot K_B \cdot \begin{bmatrix} \cos(N_P \cdot \omega \cdot t) \\ \cos\left(N_P \cdot \omega \cdot t - \dfrac{2\pi}{3}\right) \\ \cos\left(N_P \cdot \omega \cdot t + \dfrac{2\pi}{3}\right) \end{bmatrix}. \quad (4a)$$

In steady state, the stator currents are sinusoidal signals which can be written as $$i_{as} = I \cdot \sin(N_P \cdot \omega \cdot t + \alpha), \quad (4b)$$
$$i_{bs} = I \cdot \sin\left(N_P \cdot \omega \cdot t - \dfrac{2\pi}{3} + \alpha\right),$$
$$i_{cs} = I \cdot \sin\left(N_P \cdot \omega \cdot t + \dfrac{2\pi}{3} + \alpha\right),$$

where I is the current amplitude and $\alpha$ is the electrical angle between the center of the north pole of the rotor's permanent magnetic field and the north pole of the magnetic field due to the stator currents. Substituting Eqs. (4a) and (4b) into Eq. (2) results in $$W_{EM} = \int_0^\tau \left[\dfrac{3}{2} K_B \cdot N_P \cdot I \cdot \sin(\alpha) \cdot \omega\right] \cdot d\xi. \quad (5)$$

The speed of the BLDC is controlled by a ML4411 controller chip (Micro Linear Co., San Jose, Calif.), which conducts two of the three phases periodically during operation. For a three-phase motor with a four-pole permanent-magnet rotor, the ML4411 allows the angle $\alpha$ to vary only between $90° \pm 15°$. This results in a small variation of $\sin(\alpha)$ between 0.966 and 1, and therefore, Eq. (5) can be approximated by $$W_{EM} \approx \int_0^\tau \left[\dfrac{3}{2} K_B \cdot N_P \cdot I \cdot \omega\right] \cdot d\xi. \quad (6)$$

From Newton's laws of motion, $W_{MS}$ and $W_{ML}$ in Eq. (1) can be expressed [S. J. Chapman, *Electric Machinery Fundamentals*, McGraw-Hill, Book Co., 1985, pp. 5–8, incorporated by reference herein] as the mechanical energy stored in mass $$W_{MS} = \int_{\theta_1}^{\theta_2} J \cdot \dfrac{d\omega}{dt} \cdot d\theta = \int_0^\tau J \cdot \dfrac{d\omega}{dt} \cdot \dfrac{d\theta}{dt} \cdot d\xi = \int_0^\tau J \cdot \dfrac{d\omega}{dt} \cdot \omega \cdot d\xi, \quad (7)$$

and the mechanical loss due to friction $$W_{ML} = \int_{\theta_1}^{\theta_2} B \cdot \omega \cdot d\theta = \int_0^\tau B \cdot \omega^2 \cdot d\xi, \quad (8)$$

where J is the rotor's inertia and B is the viscous friction coefficient. The mechanical energy delivered to the pump can be represented by [F. M. White, *Fluid Mechanics*, 2nd Ed., McGraw-Hill, Book Co., 1986, pp. 637, incorporated by reference herein]

$$W_P = \dfrac{1}{\eta} \cdot \int_0^\tau \Delta P \cdot Q \cdot d\xi, \quad (9)$$

where $\Delta P$ is the pressure drop across the pump, Q is pump flow rate, and $\eta$ is the pump efficiency coefficient. Substituting Eqs. (6) through (9) into (1) leads to $$\int_0^\tau \left[\dfrac{3}{2} K_B \cdot N_P \cdot I \cdot \omega\right] \cdot d\xi = \quad (10)$$
$$\int_0^\tau J \cdot \dfrac{d\omega}{dt} \cdot \omega \cdot d\xi + \int_0^\tau B \cdot \omega^2 \cdot d\xi + \dfrac{1}{\eta} \cdot \int_0^\tau \Delta P \cdot Q \cdot d\xi.$$

Taking the time derivative of Eq. (10) and then dividing both sides of the resulting equation by $\omega$ leads to $$\dfrac{3}{2} K_B \cdot N_P \cdot I = J \cdot \dfrac{d\omega}{dt} + B \cdot \omega + \dfrac{1}{\eta} \cdot \left(\dfrac{\Delta P}{\omega}\right) \cdot Q \quad (11)$$

Since measuring $\Delta P$ is difficult clinically, Eq. (11) cannot be used to indicate Q directly. An empirical model of $\Delta P/(\eta \cdot \omega)$ is required which provides a good fit to the experimental data within the pump operating range. A fundamentally new expression, given by $$\dfrac{\Delta P}{\eta \cdot \omega} = K_1 \cdot \sqrt{\omega} + K_2 \cdot \omega^2, \quad (12)$$

where $K_1$ and $K_2$ are constant coefficients, was used in this work. It is shown below that this novel results in an accurate determination of the load on the pump over the normal pump operation range. Specifically, an accurate estimate of the flow rate, Q, indicated by $$\hat{Q} = \dfrac{1.5 \cdot K^* \cdot I - J \cdot \dfrac{d\omega}{dt} - B \cdot \omega}{K_1 \cdot \sqrt{\omega} + K_2 \cdot \omega^2}, \quad (13)$$

where $K^* = N_p \cdot K_B$.

In order to indicate the pump flow rate using Eq. (13), inter alia, it is necessary to identify the back EMF constant $K_B$. From Eq. (4a), the maximum induced voltage is a function of $K_B$, the number of the rotor's pole pairs, and the motor speed $$V_{MAX} = \omega \cdot N_p \cdot K_B. \quad (14)$$

If $V_{MAX}$ and $\omega$ are measured experimentally, $K_B$ can be calculated by $$K_B = V_{MAX}/(\omega \cdot N_p). \quad (15)$$

An experiment was conducted by spinning the rotor at three constant speeds and measuring the induced phase voltage. The motor speed (rad/sec) was calculated by ["ML4428 Sensorless Smart-Start BLDC PWM Motor Controller Eval Kit™", Technical Note from Micro Linear Co., San Jose, Calif., incorporated by reference herein]

$$\omega=[(120\cdot f)/(2\cdot N_p)]\cdot(2\pi/60), \quad (16)$$

where f is the frequency in Hz of the induced voltage. $K_B$ was obtained by averaging the indicated $K_B$ from each stator phase at different rotor speeds. The resulting back EMF constant was $K_B = 3.6545 \times 10^{-3}$ N·m/A.

Figure 3:
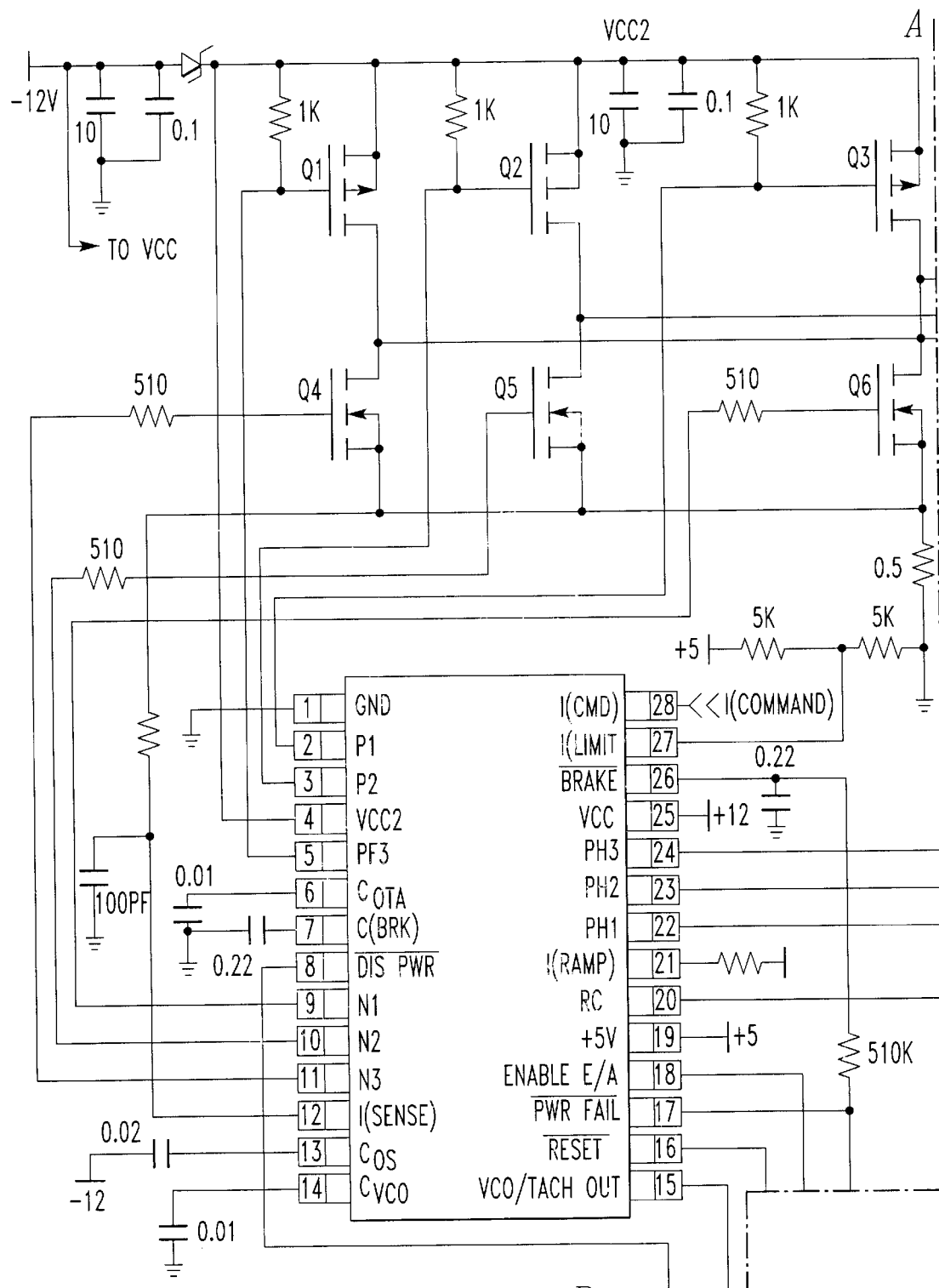
FIG. 3 is a circuit diagram for the rotary blood pump controller chip.
Figure 3A:
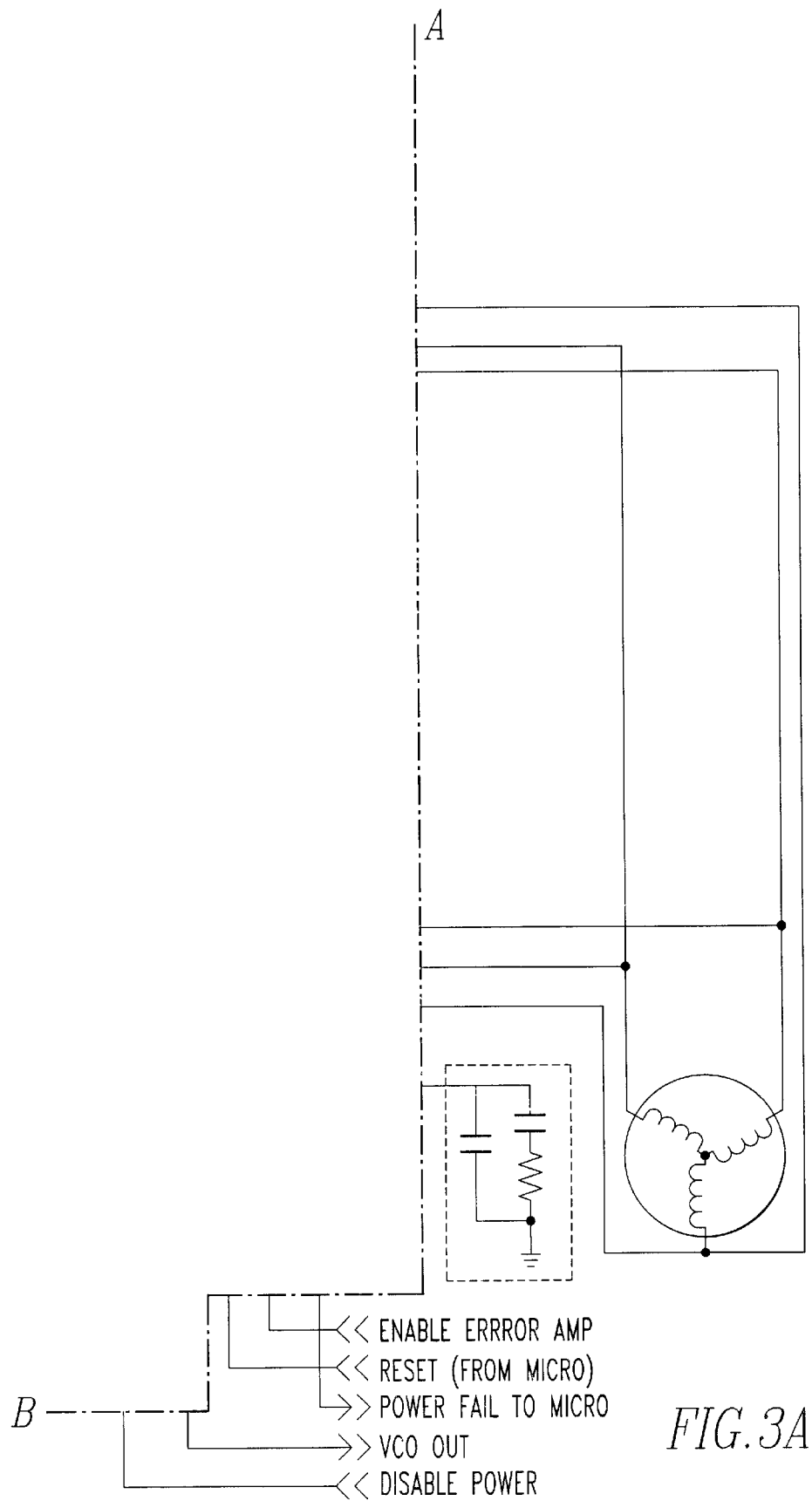

In order to indicate the blood flow rate through the AB-180 blood pump under patients' physiologic load conditions, an experiment was designed to characterize the relationship of the pump flow (Q) with the pump current and speed at different load conditions. Three experiments were conducted on a modified Penn State mock circulatory system [Rosenberg, G., W. M. Phillips, D. L. Landis, and W. S. Pierce, "Design and Evaluation of the Pennsylvania State University Mock Circulatory System", ASAIO Journal, Vol. 4, No. 2, pp. 41–49, incorporated by reference herein] with an AB-180 pump as shown in FIG. 3, simulating the patients' physiologic conditions, to generate pressure and flow data for system identification and model validation.

The mock loop comprised a simulated atrium and ventricle, a preload chamber, a Harvard Apparatus Pulsatile Blood Pump, an arterial compliance chamber, a variable resistance bed (simulating the systemic resistance), and inter-connecting fluid conduits (1"I.D. Tygon tubing). The perfusate fluid (working fluid in the mock loop) consisted of a solution of 35% glycerol and 65% saline (by volume) to simulate the viscosity of blood at 37° C. The saline was a 0.9% Sodium Chloride solution. The perfusate was maintained at room temperature (21–23° C.) because the viscosity of this mixture under these conditions approximates that of blood at body temperature [Sturn, C., W. Li, J. C. Woodard, and N. H. C. Hwang, "Fluid Mechanics of Left Ventricular Assist System Outflow Housing", ASAIO Journal, Vol. 38, pp. M225–M227, incorporated by reference herein].

In the experiment, the heart failure was simulated by setting the Harvard Pulsatile Pump to 100 beats per minute at a stroke volume of 20 cc. The pump speed was in the range of 2200 rpm to 4700 rpm. This speed range was selected because it covers the speeds (2500–4500 rpm) used clinically. The mean arterial pressure was set in the range of 50 to 100 mmHg (just outside the clinical range of 60–90 mmHg) by adjusting the systemic resistance. Left atrial pressure was varied between 5 and 20 mmHg with 5 mmHg increments by adjusting the fluid level at the preload chamber.

EXPERIMENT I
System Identification

The purpose of the first experiment was identification of the model structure and the corresponding model parameters. In this experiment, the positive displacement pump, mimicking the human left ventricle, was operated at the rate of 100 beats/min with the stroke volume of 20 ml/stroke. The left atrial pressure (LAP) was set to 15 mmHg. When the AB-180 centrifugal rotary blood pump was operating at 2200 RPM (lowest speed), the systemic resistance was adjusted such that the mean arterial pressure (MAP) reached 50 mmHg. The LAP setting was changed from 5 mmHg to 20 mmHg in 5 mmHg increments. At each LAP setting, a function generator was used to provide a sinusoidal speed reference signal. The frequency of the speed reference signal was adjusted to 0.02 Hz, 0.04 Hz, 0.08 Hz, and 0.1 Hz. The peak to peak amplitude remained fixed such that the motor speed varied between 2200 RPM and 4700 RPM. Although normal use of the AB-180 rotary blood pump is at constant speeds, sinusoidal speed references were used to ensure a proper identification of the model parameters. The pump outlet pressure, LAP, pump outflow, motor speed, and motor current were acquired through a WinDaq data acquisition system (Dataq Instruments, Akron, Ohio) at the sampling rate of 200 Hz/channel for the duration of 145 seconds.

EXPERIMENT (II)
Simulation of Systemic Circulation

In the second experiment, the positive displacement pump was operated at the rate of 120 beats/min with the stroke volume of 20 ml/stroke. LAP was set as 5 mmHg and 20 mmHg. At each of the LAP settings, the AB-180 rotary blood pump was operated at speeds from 2500 RPM to 4500 RPM (inclusive) with 500 RPM increments. At each speed, the systemic resistance was then adjusted to obtain MAP values of 50, 60, 70, 80, 90, and 100 mmHg. These settings are related to the AB-180 patients' hemodynamics conditions. Validating the flow indicator using data from these settings would provide a useful evaluation of the indicator under different physiologic conditions. The same signals as listed in the first experiment, pump outlet pressure, LAP, pump outflow, motor speed, and motor current, were acquired with the sampling rate of 200 Hz/channel for 12 seconds.

EXPERIMENT (III)
Simulation of Outflow Occlusion

In the third experiment, the experimental settings are the same as described in Experiment (II), except that the outflow conduit was clamped suddenly with a hemostat to simulate kinking the outflow conduit. The data collected in this experiment were then used to evaluate the indicator performance at the condition of outflow conduit kinking.

In order to indicate the pump flow rate using motor current and speed signals in Eq. (13), it is necessary to identify the model parameters J, B, $K_1$, and $K_2$. Substituting Eq. (12) into $$1.5K^* \cdot I = J \cdot \frac{d\omega}{dt} + B \cdot \omega + Q \cdot (K_1 \cdot \sqrt{\omega} + K_2 \cdot \omega^2), \quad (17)$$

where $K^* = N_p \cdot K_B = 7.3089 \times 10^{-3}$ N·m/A. The data sets from the first experiment were used to identify the coefficients, J, B, $K_1$, and $K_2$, in a least squares sense [Stephen, J, M. Bodson, and J. Chiasson, "Real-Time Estimation of the Parameters and Fluxes of Induction Motors", IEEE Trans. On Industry Applications, Vol. 30, No. 3, 1994, pp. 746–758, incorporated by reference herein]. The identification results are summarized in Table 1. The parametric terror index, PE, is a reliability indicator that measures the relative errors in the identified parameter values. A large PE indicates that a significant change in the parameter would not significantly degrade the matching of the data to the model. Thus, less confidence is placed on such a parameter value since it can vary from its identified value without affecting the data fit. A small PE indicates that the residual error is very sensitive to the identified parameter value, thus more confidence can be placed on the value of the identified parameter [A. J. Blauch, M. Bodson, and J. Chiasson, "High-Speed Parameter Estimation of Stepper Motors", *IEEE Trans. On Control System Technology*, Vol. 1, No. 4, 1993, pp. 270–279, incorporated by reference herein]. The small values of $PE_B$, $PE_{K1}$, and $PE_{K2}$ suggests that a high degree of confidence can be placed in the values of B, $K_1$, and $K_2$ respectively. A relatively large value of $PE_J$ indicates that the moment of inertia contains higher uncertainty. However, the effect of inertia is insignificant when the motor is running at a constant speed which is the dominant operating condition. This implies that $PE_J$ would have negligible impact on the accuracy of the model. The parameter data obtained from the data sets with four LAP settings were consistent. The error indices are less then 5%. This is with less then 10% deviation of the parameter data between data sets.

For bi-ventricular assist, the objective is to maintain a balanced blood flow between both sides of the circulatory system. Although the balance of left and right atrial pressures can be used as an index, the requirement of invasive sensors in patient's chest limits this approach clinically.

When a patient is under 100% support by the AB-180 blood pump on the systemic and pulmonary circulation, the total cardiac output can be approximated by the pump output. The speed command, $\omega_L^*$, of the left side support pump will be adjusted manually such that the flow rate, $Q_L$ from the flow indicator reaches the desired left side support flow rate, $Q_L^*$. To balance the cardiac outputs on both sides of the heart, the flow rate on the right side, $Q_R$, should be equal to the flow rate on the left side, $Q_L$. This can be achieved by using $Q_L$ as the desired flow rate on the right side $Q_R^*$, into a look-up table to determine the desired speed, $\omega_R^*$, for the right side support pump. This speed

TABLE 1

Identification Results

| LAP | J | $PE_J$ | B | $PE_B$ | $K_1$ | $PE_{K1}$ | $K_2$ | $PE_{K2}$ | $E_1$ (%) |
|---|---|---|---|---|---|---|---|---|---|
| 5 | 3.28E-06 | 0.49 | 1.07E-05 | 0.01 | 1.21E-05 | 0.07 | 1.90E-09 | 0.0442 | 0.89 |
| 10 | 3.43E-06 | 0.51 | 1.08E-05 | 0.01 | 1.08E-05 | 0.08 | 2.01E-09 | 0.0449 | 0.94 |
| 15 | 3.42E-06 | 0.51 | 1.08E-05 | 0.01 | 1.11E-05 | 0.08 | 1.98E-09 | 0.0455 | 0.95 |
| 20 | 3.76E-06 | 0.46 | 1.12E-05 | 0.01 | 1.01E-05 | 0.09 | 1.98E-09 | 0.0461 | 0.93 |
| Mean | 3.47E-06 | | 1.09E-05 | | 1.10E-05 | | 1.97E-09 | | |
| Std | 2.06E-07 | | 2.28E-07 | | 8.52E-07 | | 4.53E-11 | | |

The mean values of the parameters, obtained by averaging the identified parameter values using data from each of the four LAP settings, were used as the model parameters for flow estimation in Eq. (13). The indicated flow was close to the measured flow with error indices less then 5% in all tests.

The performance of the indicator was first validated using data from the mock loop experiment using constant pump speeds with different LAP and MAP settings. The validation results are summarized in Tables 2 and 3. The indicator was validated in 45 cases. The indicator predicted the flow rate within errors of less than 10% in 36 cases. In the other nine cases, eight of them had flow rates under 1.5 liter/min, and therefore, below the level which would be used on any patient. In other words, the large errors are outside the normal operation region of the pump. The one remaining case has an error of less than 15%.

Figure 4:
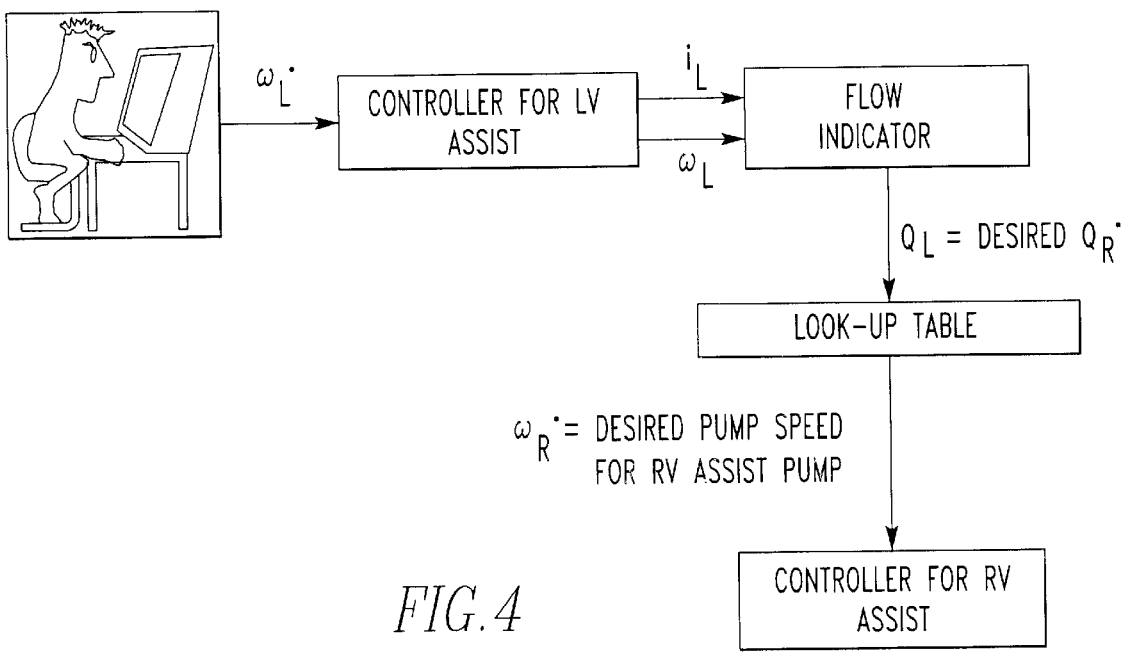
FIG. 4 is a block diagram for flow regulation for bi-ventricular assist.

When the outflow conduit was clamped by a hemostat to simulate the cannula kinking, the flow indicates decreased and were close to zero flow. Validation results of the indicator during conduit kinking are summarized in Tables 4 and 5. The estimation errors were less than 0.5 liter/min in all test conditions. These results supported that the flow indicate can be used to trigger a warning message to alert the operator of low flow conditions.

command, $\omega_R^*$, will then be sent to the speed controller of the right ventricular assist device to control the speed of the right side support pump. The block diagram of this flow regulation scheme is shown in FIG. 4.

TABLE 2

Validation of the Flow Estimator, LAP = 20 mmHg

| MAP | Pump Speed | Measured Flow | Estimated Flow | Mean Error |
|---|---|---|---|---|
| 50 | 2500 | −0.1992 | 0.355 | −0.5542 |
| 50 | 3000 | 2.6679 | 3.1542 | −0.4863 |
| 50 | 3500 | 4.7804 | 5.1209 | −0.3405 |
| 50 | 4000 | 6.3335 | 6.2548 | 0.0787 |
| 50 | 4500 | 7.7809 | 7.3587 | 0.4222 |
| 60 | 3000 | 1.6829 | 1.5196 | 0.1633 |
| 60 | 3500 | 4.0683 | 4.3882 | −0.3199 |
| 60 | 4000 | 5.7848 | 5.7788 | 0.006 |
| 60 | 4500 | 7.4455 | 7.0728 | 0.3727 |
| 70 | 3000 | 0.3364 | 0.1403 | 0.1961 |
| 70 | 3500 | 3.2016 | 3.5131 | −0.3115 |
| 70 | 4000 | 5.268 | 5.2946 | −0.0266 |
| 70 | 4500 | 7.0167 | 6.6662 | 0.3505 |
| 80 | 3500 | 2.2741 | 2.4011 | −0.127 |
| 80 | 4000 | 4.5757 | 4.6947 | −0.119 |
| 80 | 4500 | 6.4038 | 6.0945 | 0.3093 |
| 90 | 3500 | 1.2394 | 1.2344 | 0.005 |
| 90 | 4000 | 3.8931 | 4.0506 | −0.1575 |
| 90 | 4500 | 5.9635 | 5.7512 | 0.2123 |
| 100 | 3500 | −0.4682 | −0.1469 | −0.3213 |
| 100 | 4000 | 2.8537 | 2.9535 | −0.0998 |
| 100 | 4500 | 5.4256 | 5.304 | 0.1216 |

TABLE 3

Validation of the Flow Estimator, LAP = 5 mm Hg

| MAP | Pump Speed | Measured Flow | Estimated Flow | Mean Error |
|---|---|---|---|---|
| 50 | 2500 | 1.0685 | 1.3924 | −0.3239 |
| 50 | 3000 | 3.4085 | 3.9524 | −0.5439 |
| 50 | 3500 | 5.2774 | 5.4285 | −0.1511 |
| 50 | 4000 | 6.6455 | 6.5377 | 0.1078 |
| 50 | 4500 | 8.0952 | 7.5949 | 0.5003 |
| 60 | 3000 | 2.4985 | 2.8652 | −0.3667 |
| 60 | 3500 | 4.695 | 4.8953 | −0.2003 |
| 60 | 4000 | 6.2866 | 6.223 | 0.0636 |
| 60 | 4500 | 7.706 | 7.2685 | 0.4375 |
| 70 | 3000 | 1.2757 | 1.3861 | −0.1104 |
| 70 | 3500 | 3.885 | 4.1426 | −0.2576 |
| 70 | 4000 | 5.6972 | 5.6313 | 0.0659 |
| 70 | 4500 | 7.3259 | 6.9651 | 0.3608 |
| 80 | 3000 | −0.3469 | −0.0027 | 0.3496 |
| 80 | 3500 | 2.7101 | 2.8808 | −0.1707 |
| 80 | 4000 | 5.1266 | 5.144 | −0.0174 |
| 90 | 4500 | 6.8792 | 6.5544 | 0.3248 |
| 90 | 3500 | 1.7557 | 1.8435 | −0.0878 |
| 90 | 4000 | 4.5243 | 4.5474 | −0.0231 |
| 90 | 4500 | 6.301 | 6.0872 | 0.2138 |
| 100 | 3500 | 0.6117 | 0.7274 | −0.1157 |
| 100 | 4000 | 3.7723 | 3.887 | −0.1147 |
| 100 | 4500 | 5.8504 | 5.6621 | 0.1883 |

TABLE 4

Validation of the Flow Estimator with Kinked Conduit, LAP = 5 mmHg

| MAP | RPM | Measured Flow | Estimated Flow | Estimation Error (L/min) |
|---|---|---|---|---|
| 50 | 2500 | −0.0067 | 0.312 | −0.3187 |
| 50 | 3000 | −0.0108 | 0.2083 | −0.2191 |
| 50 | 3500 | −0.0098 | 0.124 | −0.1338 |
| 50 | 4000 | 0.001 | 0.224 | −0.223 |
| 50 | 4500 | −0.0092 | 0.3973 | −0.4065 |
| 60 | 3000 | −0.0047 | 0.1795 | −0.1842 |
| 60 | 3500 | −0.0063 | 0.1594 | −0.1657 |
| 60 | 4000 | −0.01 | 0.2738 | −0.2838 |
| 60 | 4500 | 0.0016 | 0.3955 | −0.3939 |
| 70 | 3000 | 0.0006 | 0.2304 | −0.2298 |
| 70 | 3500 | −0.0043 | 0.1141 | −0.1184 |
| 70 | 4000 | −0.0029 | 0.1511 | −0.154 |
| 70 | 4500 | −0.0025 | 0.3977 | −0.4002 |
| 80 | 3000 | −0.0093 | 0.1886 | −0.1979 |
| 80 | 3500 | −0.0087 | 0.1214 | −0.1301 |
| 80 | 4000 | −0.0001 | 0.2166 | −0.2167 |
| 80 | 4500 | −0.0062 | 0.3675 | −0.3737 |
| 90 | 3500 | −0.0073 | 0.1868 | −0.1941 |
| 90 | 4000 | −0.0028 | 0.1725 | −0.1753 |
| 90 | 4500 | −0.0041 | 0.3519 | −0.356 |
| 100 | 3500 | −0.0049 | 0.1649 | −0.1698 |
| 100 | 4000 | −0.0058 | 0.1973 | −0.2031 |
| 100 | 4500 | −0.0024 | 0.3602 | −0.3626 |

TABLE 5

Validation of the Flow Estimator with Kinked Conduit, LAP = 20 mmHg

| IMAP | RPM | Measured Flow | Estimated Flow | Estimation Error (L/min) |
|---|---|---|---|---|
| 50 | 2500 | −0.0059 | 0.4222 | −0.4281 |
| 50 | 3000 | −0.0071 | 0.2305 | −0.2376 |
| 50 | 3500 | −0.0016 | 0.2322 | −0.2338 |
| 50 | 4000 | −0.0039 | 0.1839 | −0.1878 |
| 50 | 4500 | 0.0008 | 0.3748 | −0.374 |
| 60 | 3000 | −0.0019 | −0.1056 | 0.1037 |
| 60 | 3500 | −0.0015 | 0.1441 | −0.1456 |
| 60 | 4000 | −0.0019 | 0.1785 | −0.1804 |
| 60 | 4500 | −0.0004 | 0.3342 | −0.3346 |
| 70 | 3000 | −0.0031 | −0.1296 | 0.1265 |
| 70 | 3500 | −0.0037 | 0.197 | −0.2007 |
| 70 | 4000 | −0.0016 | 0.1851 | −0.1867 |
| 70 | 4500 | −0.0051 | 0.3 | −0.3051 |
| 80 | 3500 | −0.0046 | 0.1928 | −0.1974 |
| 80 | 4000 | −0.0051 | 0.1935 | −0.1986 |
| 80 | 4500 | 0.0017 | 0.3471 | −0.3454 |
| 90 | 3500 | −0.0064 | 0.1781 | −0.1845 |
| 90 | 4000 | −0.0039 | 0.2064 | −0.2103 |
| 90 | 4500 | −0.0001 | 0.2958 | −0.2959 |
| 100 | 3500 | −0.0027 | 0.1001 | −0.1028 |
| 100 | 4000 | −0.0027 | 0.1989 | −0.2016 |
| 100 | 4500 | −0.005 | 0.3329 | −0.3379 |

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for moving blood in a patient comprising:
a blood pump, said blood pump having a moving mechanism which contacts blood and imparts energy to the blood to move the blood for the patient at a desired flow rate, and a mechanism for causing the moving mechanism to move the blood, said causing mechanism engaged with said moving mechanism, said causing mechanism receiving energy to power the causing mechanism; and
a flow indicator connected to the blood pump to identify the flow of blood through the pump based only on an energy balance between the energy imparted to the blood by the moving mechanism and the energy received by the causing mechanism.

2. An apparatus as described in claim 1 wherein the pump is a rotary pump and the causing mechanism includes a motor.

3. An apparatus as described in claim 2 wherein the rotary pump is a centrifugal pump.

4. An apparatus as described in claim 3 wherein the energy powering the causing mechanism is current, and wherein the flow indicator identifies the flow of blood with the current and speed of the motor based on the energy balance between the energy imparted to the blood by the moving mechanism and the energy received by the causing mechanism.

5. An apparatus as described in claim 4 wherein the flow rate, Q, of the blood through the pump is defined by $$Q = \frac{1.5 \cdot K^* \cdot I - J \cdot \frac{d\omega}{dt} - B \cdot \omega}{K_1 \cdot \sqrt{\omega} + K_2 \cdot \omega^2},$$

where B is the viscous friction coefficient, $K_1$ and $K_2$ are constant coefficients, J is the motors inertia, I is the current amplitude, and $\omega$ is the rotor angular velocity. $K^* = N_p K_B$ where $N_p$ is the number of pole pairs and $K_B$ is back-emf constant.

6. An apparatus as described in claim 5 wherein the moving mechanism includes an impeller.

7. An apparatus as described in claim 6 wherein the motor includes a brushless DC motor.

8. An apparatus as described in claim 7 wherein the motor includes a stator and a rotor disposed in the stator, said impeller connected to the rotor.

9. An apparatus as described in claim 8 wherein the flow indicator can detect retrograde flow, and wherein the pump includes conduits and the flow indicator which can detect conduit kinking.

10. An apparatus as described in claim 9 wherein the motor is a three-phase permanent magnetic brushless DC motor.

11. An apparatus as described in claim 10 wherein the flow indicator utilizes a curve fit to identify flow.

12. An apparatus as described in claim 11 wherein the flow indicator utilizes a table look up based on the curve fit to identify blood flow.

13. A method for determining blood flow in a patient comprising the steps of:

provide energy to a blood pump to operate the pump;

imparting energy to blood for the patient with the blood pump at a desired flow rate; and identifying the flow rate only by balancing the energy imparted to the blood with energy provided to the pump.

14. A method as described in claim 13 wherein the providing step includes the step of providing current to a rotary blood pump and the identifying step includes the step of measuring the current and speed of the pump.

15. A method as described in claim 14 wherein the controller indicates the flow rate according to $$Q = \frac{1.5 \cdot K^* \cdot I - J \cdot \frac{d\omega}{dt} - B \cdot \omega}{K_1 \cdot \sqrt{\omega} + K_2 \cdot \omega^2},$$

where B is the viscous friction coefficient, $K_1$ and $K_2$ are constant coefficients, J is the motors inertia, I is the current amplitude, and $\omega$ is the rotor angular velocity.

16. An apparatus for flow regulation for heart assist comprising:

a left assist blood pump to assist in the moving of blood through the left part of the heart;

a right assist blood pump to assist in the moving of blood through the right part of the heart;

a controller for controlling the left assist blood pump connected to the left assist blood pump;

a flow indicator for indicating flow through the left part of the heart connected to the left assist pump controller; and a mechanism for controlling the right assist blood pump connected to the right assist pump.

17. A method for flow regulation for assist comprising the steps of:

setting a speed of a left assist rotary blood pump;

controlling the left assist rotary blood pump with a controller for left assist rotary pump based on the speed;

indicating the flow of blood through the left ventricle with a flow indicator based on the speed and current provided to the left assist rotary blood pump;

identifying a desired speed for a right assist rotary blood pump from the flow of the blood through the left assist rotary blood pump; and controlling the right assist rotary blood pump with a right ventricular assist controller based on the desired speed.

* * * * *